United States Patent
Kohn et al.

(10) Patent No.: US 7,056,493 B2
(45) Date of Patent: *Jun. 6, 2006

(54) RADIO-OPAQUE POLYMER BIOMATERIALS

(75) Inventors: Joachim B Kohn, Highland Park, NJ (US); Durgadas Bolikal, Edison, NJ (US); Sanyog M Pendharkar, Old Bridge, NJ (US)

(73) Assignee: Rutgers,The State University, New Brunswick, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/691,750

(22) Filed: Oct. 23, 2003

(65) Prior Publication Data

US 2004/0086461 A1 May 6, 2004

Related U.S. Application Data

(60) Continuation of application No. 10/288,076, filed on Nov. 5, 2002, now Pat. No. 6,852,308, which is a division of application No. 09/554,027, filed as application No. PCT/US98/23777 on Nov. 6, 1998, now Pat. No. 6,475,477.

(60) Provisional application No. 60/064,905, filed on Nov. 7, 1997.

(51) Int. Cl.
*A61K 49/04* (2006.01)

(52) U.S. Cl. .................. 424/9.4; 424/1.11; 424/9.1; 424/78.08; 424/78.01; 424/1.65; 424/9.6; 528/176

(58) Field of Classification Search ............... 424/1.11, 424/1.65, 9.1, 9.6, 78.01, 78.02, 78.03, 78.04, 424/78.05, 78.08, 78.17, 78.18; 528/176, 528/182, 196, 203, 204, 206, 272, 332; 525/432, 525/433, 434, 454, 467; 568/303, 700; 560/40
See application file for complete search history.

(56) References Cited

U.S. PATENT DOCUMENTS

| | | | | |
|---|---|---|---|---|
| 5,587,507 A | * | 12/1996 | Kohn et al. | 560/40 |
| 5,670,602 A | * | 9/1997 | Kohn et al. | 528/176 |
| 6,475,477 B1 | * | 11/2002 | Kohn et al. | 424/78.08 |
| 6,602,497 B1 | * | 8/2003 | Kohn et al. | 424/78.08 |
| 6,852,308 B1 | * | 2/2005 | Kohn et al. | 424/9.6 |
| 2004/0086461 A1 | * | 5/2004 | Kohn et al. | 424/9.451 |

* cited by examiner

Primary Examiner—D. L. Jones
(74) Attorney, Agent, or Firm—Synnestvedt & Lechner, LLP

(57) ABSTRACT

Iodinated and/or brominated derivatives of aromatic dihydroxy monomers are prepared and polymerized to form radio-opaque polymers. The monomers may also be copolymerized with other dihydroxy monomers. The iodinated and brominated aromatic dihydroxy monomers can be employed as radio-opacifying, biocompatible non-toxic additives for other polymeric biomaterials. Radio-opaque medical implants and drug delivery devices for implantation prepared from the polymers of the present invention are also disclosed.

34 Claims, 1 Drawing Sheet

RADIO-OPAQUE POLYMER BIOMATERIALS

CROSS REFERENCE TO RELATED APPLICATION

This application is a continuation of U.S. patent application Ser. No. 10/288,076 (pending) which was filed on Nov. 5, 2002 with the United States Patent and Trademark Office, which application, in turn, is a Divisional of U.S. patent application Ser. No. 09/554,027 filed Jul. 3, 2000 which issued as U.S. Pat. No. 6,475,477 on Nov. 5, 2002, and which claims priority benefit under 35 U.S.C. §371 of PCT/US98/23777 filed Nov. 6, 1998, which, in turn, claims priority benefit of U.S. Provisional Patent Application No. 60/064,905, filed on Nov. 7, 1997. The disclosures of the aforementioned applications are incorporated herein by reference.

GOVERNMENT LICENSE RIGHTS

The U.S. Government has a paid-up license in this invention and the right in limited circumstances to require the patent owner to license others on reasonable terms as required by the terms of Grant Nos. GM-39455 and GM-49849 awarded by the National Institutes of Health.

TECHNICAL FIELD

The present invention relates to radio-opaque biodegradable polycarbonates and polyarylates and the block copolymers thereof with poly(alkylene oxides). In particular, the present invention relates to polycarbonates and polyarylates and the poly(alkylene oxide) block copolymers thereof that are radio-opaque as a consequence of being homopolymers and copolymers of dihydroxy monomers having iodinated or brominated aromatic rings as part of their structure.

BACKGROUND OF THE INVENTION

Diphenols are monomeric starting materials for polycarbonates, polyiminocarbonates, polyarylates, polyurethanes, and the like. Commonly owned U.S. Pat. Nos. 5,099,060 and 5,198,507 disclose amino acid-derived diphenol compounds, useful in the polymerization of polycarbonates and polyiminocarbonates. The resulting polymers are useful as degradable polymers in general and as tissue-compatible bioerodible materials for medical uses, in particular. The suitability of these polymers for their end use application is the result of their polymerization from diphenols derived from the naturally occurring amino acid, L-tyrosine. The disclosures of U.S. Pat. Nos. 5,099,060 and 5,198,507 are hereby incorporated by reference. These previously-known polymers are strong, water-insoluble materials that can best be used as structural implants.

The same monomeric L-tyrosine derived diphenols are also used in the synthesis of polyarylates as described in commonly owned U.S. Pat. No. 5,216,115 and in the synthesis of poly(alkylene oxide) block copolymers with the aforementioned polycarbonates and polyarylates, which is disclosed in commonly owned U.S. Pat. No. 5,658,995. The disclosures of U.S. Pat. Nos. 5,216,115 and 5,658,995 are also hereby incorporated by reference.

Commonly owned International Application No. WO 98/36013 discloses dihydroxy monomers prepared from α-, β- and hydroxy acids and derivatives of L-tyrosine that are also useful starting materials in the polymerization of polycarbonates, polyiminocarbonates, polyarylates, and the like. The preparation of polycarbonates, polyarylates and polyiminocarbonates from these monomers is also disclosed. The disclosure of International Application No. WO 98/36013 is also hereby incorporated by reference.

Synthetic, degradable polymers are currently being evaluated as medical implants in a wide range of applications, such as orthopedic bone fixation devices, drug delivery systems, cardiovascular implants, and scaffolds for the regeneration/engineering of tissue. Such polymers, when used as implants, are non-traceable without invasive procedures. A radio-opaque polymer would offer the unique advantage of being traceable via routine X-ray imaging. The fate of such an implant through various stages of its utility could be followed without requiring invasive surgery.

Davy et al., *J. Dentist.*, 10(3), 254–64 (1982), disclose brominated derivatives of poly(methyl methacrylate) that are radio-opaque. Copolymerization with non-brominated analogs was required to obtain the thermomechanical properties required for its desired use as a denture base. Only in a small range of certain percentage concentrations of the bromo-derivative does the material exhibit acceptable thermomechanical properties. In addition, there is no disclosure that the materials exhibiting acceptable properties remain biocompatible following the addition of bromine to the polymer structure. In contrast to the polymers disclosed in this application, the brominated poly(methyl methacrylates) do not degrade. However, because the bromine atoms are located on the aliphatic ester side chain, upon side chain ester cleavage, the polymer loses its radio-opacity.

Horak et al., *Biomater.*, 8, 142–5 (1987), disclose the triiodobenzoic acid ester of poly(2-hydroxyethyl methacrylate) to be useful as a radio-opaque X-ray imaging marker compound. The iodine content was reported to affect the contrast, volume, mechanical properties and hydrophobicity of the polymer. A proper balance of properties, including radio-contrast and swellability, was achieved through optimization of the iodine content. Again, this material does not degrade through the main chain and loses radio-opacity upon side chain ester cleavage because the iodine atoms are located on the ester side chain.

Cabasso et al., *J. Appl. Polym. Sci.*, 38, 1653–66 (1989), disclose the preparation of a radio-opaque miscible polymer coordination complex of poly(methyl methacrylate) and a uranium salt, uranyl nitrate. The polymer does not degrade through the main chain and the biocompatibility of the uranyl nitrate complex is not reported, nor has the long-term stability of the complex in vivo been established.

Cabasso et al., *J. Appl. Polym. Sci.*, 41, 3025–42 (1990), discloses the preparation of radio-opaque coordination complexes of bismuth bromide and uranyl hexahydrate with polymers prepared from acrylated phosphoryl esters containing 1,3-dioxalane moieties derived from polyols such as glycerol, D-mannitol, D-sorbitol, pentaerythritol and dipentaerythritol. The phosphoryl group was selected to provide stronger coordinating sites for the bismuth and uranium salts and to impart adhesive properties toward hard tissues. Preliminary biocompatibility data indicated satisfactory performance, but the polymer does not degrade through the main chain and the long-term stability of the complex in vivo is not reported.

Jayakrishnan et al., *J. Appl. Polym. Sci.*, 44, 743–8 (1992), discloses radio-opaque polymers of triiodophenyl methacrylate and of the iothalamic ester of 2-hydroxyethyl methacrylate. Polymers of useful molecular weight were not obtained, attributable to the presence of bulky iodine atoms in the monomer side chain. It was possible to obtain copolymers with non-iodinated analogs in the presence of crosslinking agents, such that up to 25% of the iodinated monomer could be incorporated. Preliminary biocompatibility data indicated that the presence of triiodophenyl methacrylate caused blood hemolysis. In addition, the materials also do not degrade through the main chain, and in the event of side chain ester cleavage, would lose their radio-opacity because of the iodine atoms being located in the side chain.

Kraft et al., Biomater., 18 31–36 (1997), discloses the preparation of radio-opaque iodine-containing poly(methyl methacrylates). The monomers were ortho-and para-iodo and 2,3,5-triiodobenzoic acid esters of 2-hydroxymethyl methacrylate, and the para-iodophenol ester of methyl methacrylic acid. The monomers were copolymerized with one or more non-iodinated analogs and a small amount of crosslinkers to produce polymer hydrogels with varying iodine contents. It was reported that the hydrogels were well tolerated by subcutaneous tissues and that the presence of iodine did not severely alter the swellability of the hydrogel. No tissue necrosis, abscess formation or acute inflammation was observed, although all implants were surrounded by a fibrous capsule. However, these materials also do not degrade through the main polymer chain, and upon side chain ester cleavage, lose radio-opacity because of the iodine atoms being located in the ester side chain.

Currently, no technology is available to provide radio-opaque polymers that degrade through the main polymer chain, such as the above-discussed tyrosine-derived polymers. For their intended use as medical implants, radio-opaqueness is a valuable property. A need exists for radio-opaque polymers that degrade through the main polymer chains, such as the tyrosine-derived polymers discussed above.

SUMMARY OF THE INVENTION

These needs are met by the present invention. It has now been found that iodination or bromination of the aromatic rings of dihydroxy monomers renders the resulting polymers radio-opaque. Significantly, the resulting polymers exhibit good mechanical and engineering properties while degrading into relatively non-toxic products after implantation in vivo.

In general, the ability of a species to absorb X-rays is related directly to atomic number and is approximated by the relationship.

$$m = kl^3 Z^4 + 0.2$$

wherein m is the absorption coefficient, l is the wavelength of the incident X-ray, Z is the atomic number of the absorbing species and k is the proportionality constant. Iodine and bromine atoms, because of their high mass, scatter X-rays and impart radio-opaqueness. This is highly significant and allows clinicians to visualize any implanted device prepared from a radio-opaque polymer by simple X-ray imaging.

Thus, iodinated and/or brominated derivatives of dihydroxy monomers may be prepared and polymerized to form radio-opaque polycarbonates and polyarylates. These monomers may also be copolymerized with poly(alkylene oxides) and other dihydroxy monomers. In addition, the iodinated and brominated dihydroxy monomers can be employed as radio-opacifying, biocompatible non-toxic additives for other polymeric biomaterials.

Therefore, according to one aspect of the present invention, a diphenolic radio-opacifying, biocompatible, non-toxic additive for polymeric biomaterials is provided having the structure of Formula I:

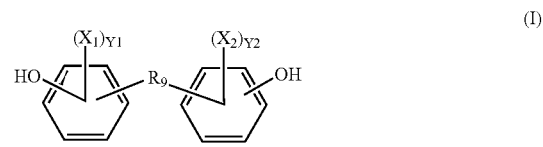

Formula I represents a diphenol compound substituted with at least one bromine or iodine atom, wherein each $X_1$, and $X_2$ is independently an iodine or bromine atom, Y1 and Y2 are independently between zero and two, inclusive, and $R_9$ is an alkyl, aryl or alkylaryl group with up to 18 carbon atoms. Preferably, $R_9$ contains as part of its structure a carboxylic acid group or a carboxylic acid ester group, wherein the ester is selected from straight and branched alkyl and alkylaryl groups containing up to 18 carbon atoms in addition to the rest of the $R_9$ structure, and ester derivatives of biologically and pharmaceutically active compounds covalently bonded to the diphenol, which are also not included among the carbons of $R_9$. $R_9$ can also contain non-carbon atoms such as iodine, bromine, nitrogen and oxygen.

In particular, $R_9$ can have a structure related to derivatives of the natural amino acid tyrosine, cinnamic acid, or 3-(4-hydroxyphenyl) propionic acid. In these cases, $R_9$ assumes the specific structure shown in Formula II:

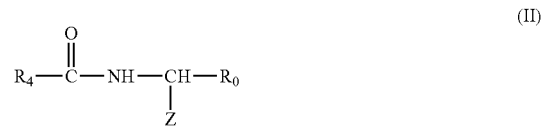

$R_0$ is selected from (—CH=CH—), (—CHJ$_1$-CHJ$_2$-) and (—CH$_2$—)$_d$ and $R_4$ is selected from (—CH=CH—), (—CHJ$_1$-CHJ$_2$-) and (—CH$_2$—)$_2$, in which a and d are independently 0 to 8, inclusive, and J$_1$ and J$_2$ are independently Br or I. Z is H, a free carboxylic acid group, or an ester or amide thereof Z preferably is a pendent group having a structure according to Formula IV:

wherein L is selected from hydrogen and straight and branched alkyl and alkylaryl groups containing up to 18 carbon atoms and derivatives of biologically and pharmaceutically active compounds covalently bonded to the dihydroxy compound.

Z can also be a pendent group having a structure according to Formula IVa:

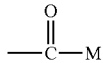
(IIIa)

According to another aspect of the present invention, a radio-opacifying, biocompatible, non-toxic dihydroxy additive for polymeric biomaterials is provided having the structure of Formula III:

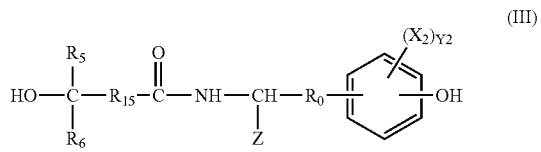
(III)

Formula III represents a dihydroxy compound substituted with at least one bromine or iodine atom and having a structure related to derivatives of tyrosine joined by way of an amide linkage to an α-, β- or γ-hydroxy acid or derivative thereof. Each $X_2$ is independently an iodine or bromine atom; Y2 is 1 or 2; $R_5$ and $R_6$ are each independently selected from H, bromine, iodine and straight and branched alkyl groups having up to 18 carbon atoms; $R_0$ is $(-CH_2-)_d$, $-CH=CH-$ or $(-CHJ_1-CHJ_2-)$ and $R_{15}$ is $(-CH_2-)_m$, $CH=CH-$ or $(-CHJ_1-CHJ_2-)$, wherein $J_1$ and $J_2$ are independently Br or I and d and m are independently between 0 and 8, inclusive. Z is the same as described above with respect to Formula II.

According to another aspect of the present invention, radio-opaque biocompatible polymers are provided having monomeric repeating units defined in Formulae Ia and IIIa:

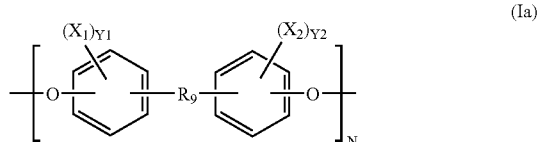
(Ia)

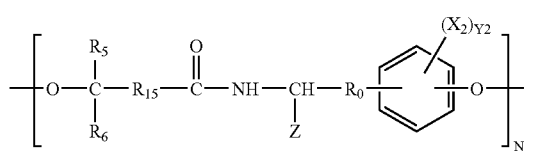
(IIIa)

Formula Ia represents a diphenolic unit wherein $X_1$, $X_2$, Y 1, Y2 and $R_9$ are the same as described above with respect to Formula I. Formula IIIa represents an aromatic dihydroxy unit wherein $X_2$, Y2, $R_0$, $R_5$, $R_6$, $R_{15}$ and Z are the same as described above with respect to Formula III.

wherein M is selected from —OH, —NH—NH$_2$, —O—R$_{10}$—NH$_2$, —O—R$_{10}$—OH, —NH—R$_{10}$—NH$_2$, —NH—R$_{10}$—OH,

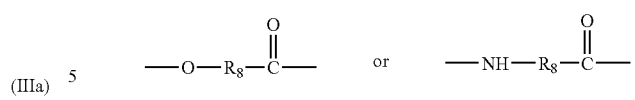

a C-terminus protecting group and a derivative of a biologically or pharmaceutically active compound covalently bonded to the pendent functional group by means of amide bond, wherein in the underivatized biologically of pharmaceutically active compound a primary or secondary amine is present in the position of the amide bond in the derivative.

Z can also be a pendent group having a structure represented by Formula IVb:

(IIIb)

wherein M is a derivative of a biologically or pharmaceutically active compound covalently bonded to the pendent functional group by means of $R_3$, wherein $R_3$ is a linkage selected from —NH—NH— in the case when in the underivatized biologically or pharmaceutically active compound an aldehyde or ketone is present at the position links to the pendent functional groups by means of $R_3$; and —NH—NH—, —NH—R$_{10}$—NH—, —O—R$_{10}$—NH—, —O—R$_{10}$—O— or —NH—R$_{10}$—O— in the case when in the underivatized biologically or pharmaceutically active compound a carboxylic acid is present in the position linked to the pendent functional group by means of $R_3$; and

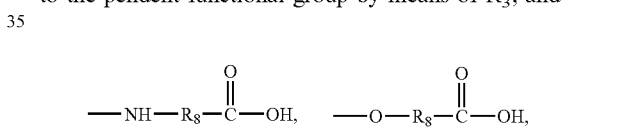

in the case when in the underivatized biologically or pharmaceutically active compound a primary or secondary anine or primary hydroxyl is present in the position linked to the pendent functional group by means of $R_3$.

$R_{10}$ is selected from alkyl groups containing from 2 to 6 carbon atoms, aromatic groups, α-, β-, γ- and ω-amino acids and peptide sequences.

Copolymers in accordance with the present invention have a second dihydroxy unit defined in Formulae Ib or IIIb.

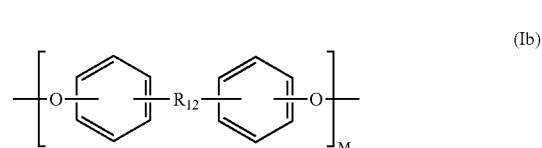
(Ib)

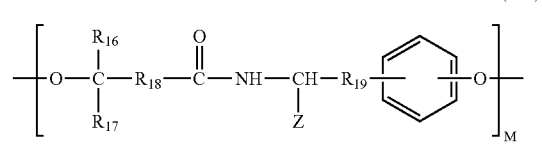
(IIIb)

In the diphenolic subunit of Formula Ib, $R_{12}$ is an alkyl, aryl or alkylaryl groupwithupto 18 carbon atoms, preferably substituted with a pendent free carboxylic acid group or an ester or amide thereof, wherein the ester or amide is selected from straight and branched alkyl and alkylaryl esters containing up to 18 carbon atoms, in addition to the rest of the $R_{12}$ structure, and derivatives of biologically and pharmaceutically active compounds covalently bonded to the polymer, which are also not included among the carbons of $R_{12}$. $R_{12}$ can also contain non-carbon atoms such as nitrogen and oxygen. In particular, $R_2$ can have a structure related to derivatives of the natural amino acid tyrosine, cinnamic acid, or 3'(4'-hydroxyphenyl) propionic acid.

For derivatives of tyrosine, 3'(4'-hydroxyphenyl) propionic acid and cinnamic acid, $R_{12}$ assumes the specific structure shown in Formula II in which $R_0$ is —CH=CH— or $(-CH_2-)_d$ and $R_4$ is —CH=CH— or $(-CH_2-)_a$, in which a and d are independently 0 to 8, inclusive. Z is the same as described above with respect to Formula II.

In the dihydroxy subunit of Formula IIIb, $R_{16}$ and $R_{17}$ are each independently selected from H or straight or branched alkyl groups having up to 18 carbon atoms; $R_{18}$ is —CH=CH— or $(-CH_2-)_d$ and $R_{19}$ is —CH=CH— or $(-CH_2-)_e$, in which d and e are independently between 0 and 8, inclusive. Z is again the same as described above with respect to Formula II.

Some polymers of this invention may also contain blocks of poly(alkylene oxide) as defined in Formula VII. In Formula VII, $R_7$ is independently an alkylene group containing up to 4 carbon atoms and k is between about 5 and about 3,000.

$$-(O-R_7)_k-O- \qquad (VII)$$

A linking bond, designated as "A" is defined to be either

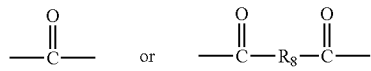

wherein $R_8$ is selected from saturated and unsaturated, substituted and unsubstituted alkyl, aryl and alkylaryl groups containing up to 18 carbon atoms. Thus, polymers in accordance with the present invention have the structure of Formulae VIII and VIIIa:

In both formulae, f and g are the molar ratios of the various subunits. The range of f and g can be from 0 to 0.99. It is understood that the presentation of both formulae is schematic and that the polymer structures represented are true random copolymers where the different subunits can occur in any random sequence throughout the polymer backbone. Formulae VIII and VIIIa provide a general chemical description of polycarbonates when A is

Formulae VIII and VIIIa provide a general description of polyarylates when A is

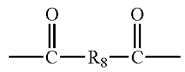

Furthermore, several limiting cases can be discerned: When g=0, the polymer contains only iodine or bromine-substituted monomeric repeating units. If g is any fraction greater than 0 but smaller than 1, a copolymer is obtained that contains a defined ratio of monomeric repeating units substituted with bromine or iodine and monomeric repeating units that are bromine- and iodine-free.

If f=0, the polymer will not contain any poly(alkylene oxide) blocks. The frequency at which poly(alkylene oxide) blocks can be found within the polymer backbone increases as the value of f increases.

The radio-opaque bromine- and iodine-substituted dihydroxy compounds of the present invention meet the need for biocompatible biodegradable additives that are miscible with radio-opaque polymeric biomaterials and enhance the radio-opacity of the polymeric materials. Therefore, the present invention also includes the radio-opaque bromine- and iodine-substituted dihydroxy compounds of the present invention, physically admixed, embedded in or dispersed in a biocompatible biodegradable polymer matrix. Preferably,

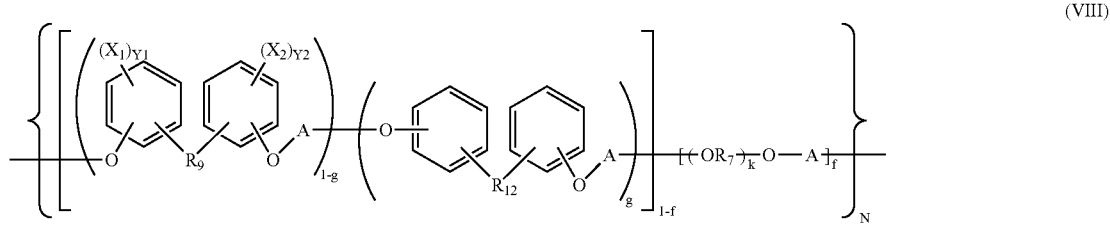

(VIII)

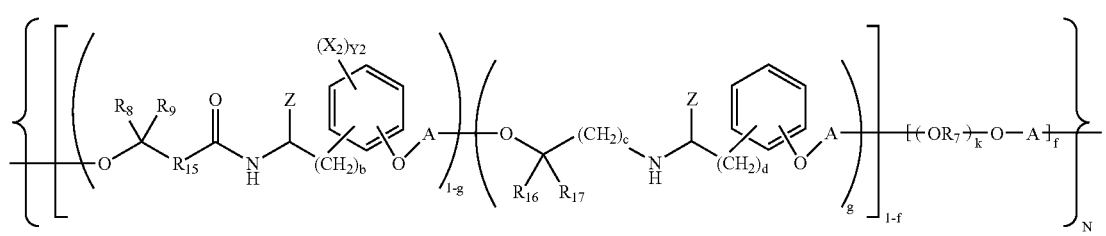

(VIIIa)

the dihydroxy compound is an analogue of a monomeric repeating unit of the matrix polymer.

The bromine- and iodine-containing polymers of the present invention also meet the need for radio-opaque processible biocompatible biodegradable polymers, the radio-opacity of which is not affected by anything other than degradation of the main polymer chain. Therefore, the present invention also includes implantable medical devices containing the radio-opaque polymers of the present invention. The radio-opaque polymers of the present invention thus find application in areas where both structural solid materials and water-soluble materials are commonly employed.

Polymers in accordance with the present invention may be prepared having good film-forming properties. An important phenomena observed for the polymers of the present invention having poly(alkylene oxide) segments is the temperature dependent face transition of the polymer gel or the polymer solution in aqueous solvents. As the temperature increases, the gel of the polymers undergo a face transition to a collapsed state, while polymer solutions precipitate at a certain temperature or within certain temperature ranges. The polymers of the present invention having poly(alkylene oxide) segments, and especially those that undergo a phase transition at about 30° to 40° C. on heating can be used as biomaterials for drug release and clinical implantation materials. Specific applications include films and sheets for the prevention of adhesion and tissue reconstruction.

Therefore, in another embodiment of the present invention, radio-opaque poly(alkylene oxide) block copolymers of polycarbonates and polyarylates may be formed into a sheet or a coating for application to exposed injured tissues for use as barrier for the prevention of surgical adhesions as described by Urry et al., *Mat. Res. Soc. Symp. Proc.*, 292, 253–64 (1993). Placement of the radio-opaque polymer sheets of the present invention may be followed by X-ray imaging without invasive surgery. This is particularly useful with endoscopic surgery. Therefore, another aspect of the present invention provides a method for preventing the formation of adhesions between injured tissues by inserting as a barrier between the injured tissues a sheet or a coating of the radio-opaque poly(alkylene oxide) block copolymers of polycarbonates and polyarylates of the present invention.

The poly(alkylene oxide) segments decrease the surface adhesion of the polymers of the present invention. As the value of f in Formulae VIII and VIIIa increases, the surface adhesion decreases. Polymer coating containing poly(alkylene oxide) segments according to the present invention may thus be prepared that are resistant to cell attachment and useful non-thrombogenic coatings on surfaces in contact with blood. Such polymers also resist bacterial adhesion in this, and in other medical applications as well. The present invention therefore includes blood contacting devices and medical implants having surfaces coated with the polymers of Formulae VIII and VIIIa in which f is greater than 0. The surfaces are preferably polymeric surfaces. Methods according to the present invention include implanting in the body of the patient a blood-contacting device or medical implant having a surface coated with the above-described polymers of the present invention containing poly(alkylene oxide) segments.

Blood contacting or implantable medical devices formed from the polymers of the present invention are also included in the scope of the present invention as well. Such polymers may or may not have poly(alkylene oxide) segments.

The present invention also includes microspheres of the radio-opaque polymers of the present invention, useful as X-ray contrast agents or as drug delivery systems, the location of which can be traced by X-ray imaging. For purposes of the present invention, the term "X-ray imaging" is defined as including essentially any imaging technique employing X-rays, including the extensively practiced procedures of radiography, photography and Computerized Axial Tomography Scans (CAT scans). Methods in accordance with the present invention for the preparation of drug delivery systems can also be employed in the preparation of radio-opaque microspheres for drug delivery.

In another embodiment of the present invention, the polymers are combined with a quantity of a biologically or pharmaceutically active compound sufficient for effective site-specific or systemic drug delivery as described by Gutowska et al., *J. Biomater. Res.*, 29, 811–21 (1995), and Hoffman, *J. Controlled Release*, 6, 297–305 (1987). The biologically or pharmaceutically active compound may be physically admixed, embedded in or dispersed in the polymer matrix as if it were not a radio-opaque polymer, eliminating the need for radio-opaque filler materials, thereby increasing the drug loading capacity of the matrix polymer.

Another aspect of the present invention provides a method for site-specific or systemic drug delivery by implanting in the body of a patient in need thereof an implantable drug delivery device containing a therapeutically effective amount of a biologically or pharmaceutically active compound in combination with a radio-opaque polymer of the present invention. As noted above, derivatives of biologically and pharmaceutically active compounds can be attached to the polymer backbone by covalent bonds, which provides for the sustained release of the biologically or pharmaceutically active compound by means of hydrolysis of the covalent bond with the polymer backbone.

By varying the value off in the polymers of Formulae VIII and VIIIa, the hydrophilic/hydrophobic ratios of the polymers of the present invention can be attenuated to adjust the ability of the polymer coatings to modify cellular behavior. Increasing levels of poly(alkylene oxide) inhibits cellular attachment, migration and proliferation, increasing the amount of pendent free carboxylic acid group promotes cellular attachment, migration and proliferation. Therefore, according to yet another aspect of the present invention, a method is provided for regulating cellular attachment, migration and proliferation by contacting living cells, tissues, or biological fluids containing living cells with the polymers of the present invention.

A more complete appreciation of the invention and many other intended advantages can be readily obtained by reference to the following detailed description of the preferred embodiment and claims, which disclose the principles of the invention and the best modes which are presently contemplated for carrying them out

BEST MODES OF CARRYING OUT THE INVENTION

Figure 1:
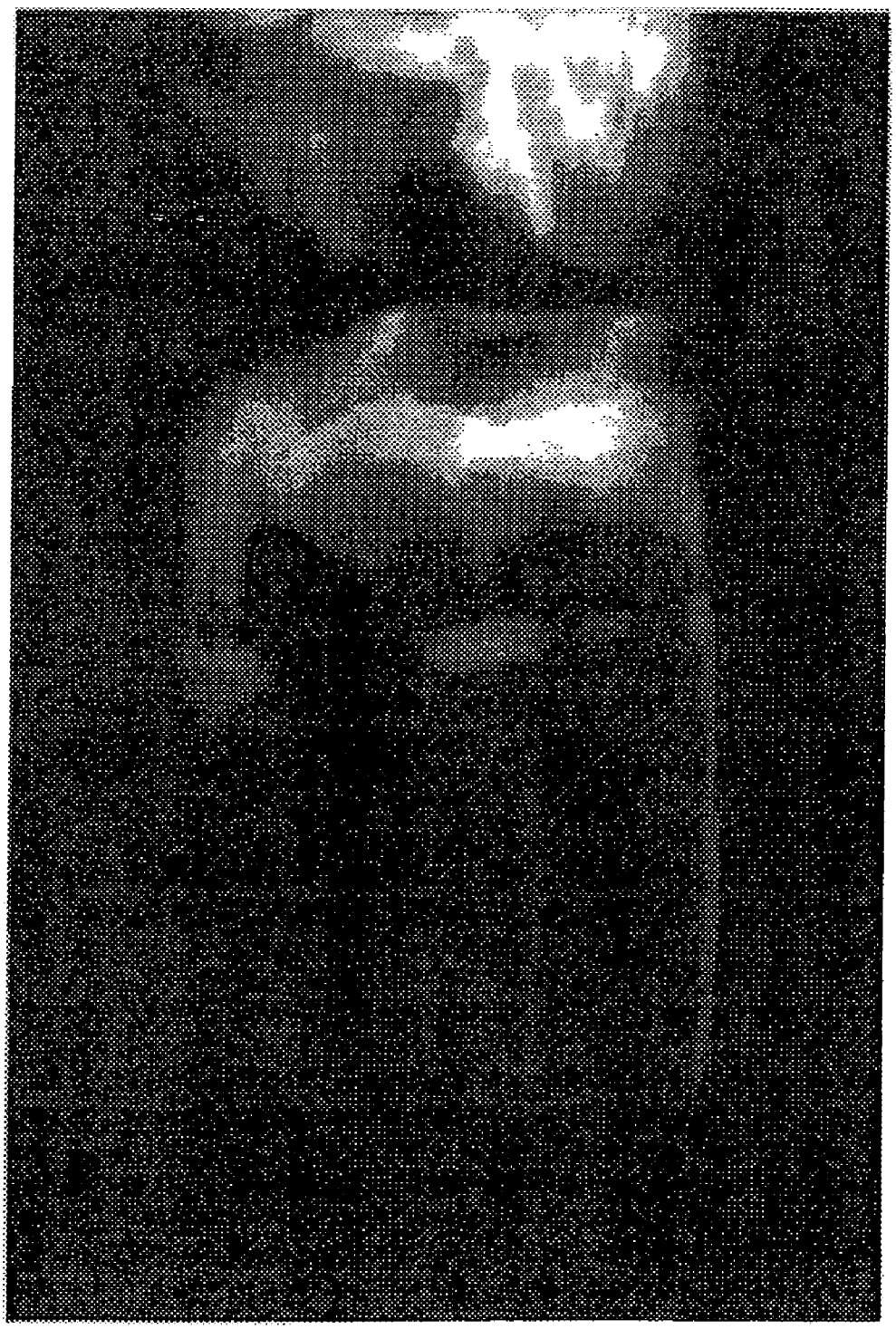
FIG. 1 is an X-ray image of a radio-opaque polymer pin according to the present invention implanted into a section of a rabbit femur.

The present invention provides radio-opaque polycarbonates and polyarylates, as well as poly(alkylene oxide) block copolymers thereof, in which the radio-opacity is derived from bromine- and iodine-substitution of some or all of the aromatic rings in the polymer backbone. The bromine- and iodine-substituted polymers are prepared by brominating or iodinating a pre-monomer compound prior to synthesis of the dihydroxy monomer. The dihydroxy monomer is subsequently polymerized by established procedures, alone, or in combination with dihydroxy compounds that are not bromine- or iodine-substituted.

In particular, the bromine- and iodine-substituted dihydroxy compounds include diphenols having the structure of Formula I wherein $R_9$ is the same as described above with respect to Formula I. The diphenols preferably have the structure of Formula II. Among the preferred diphenols are compounds in which $R_9$ has the structure of Formula II in which $R_4$ is —$CH_2$— or —$CHJ_1$-$CHJ_2$- and $R_0$ is —$CH_2$— or —$CH_2$—$CH_2$—. Most preferably, $R_4$ is —$CHJ_1$-$CHJ_2$- and $R_0$ is —$CH_2$—. These most preferred compounds are bromine- and iodine-substituted tyrosine dipeptide analogues known as desaminotyrosyl-tyrosine, and the alkyl and alkylaryl esters thereof. In this preferred group, the diphenols can be regarded as derivatives of tyrosyl-tyrosine dipeptides from which the N-terminal amino group has been removed.

Diphenol compounds that are not bromine- or iodine-substituted have the structure of Formula Ic:

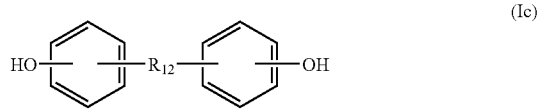

(Ic)

wherein $R_{12}$ is the same as described above with respect to Formula Ib. $R_{12}$ preferably has the structure shown in Formula II in which $R_0$ is —CH=CH— or (—$CH_2$—)$_d$ and $R_4$ is —CH=CH— or (—$CH_2$—)$_2$, in which a and d are independently 0 to 8.

Methods for preparing the diphenol monomers in which $R_9$ or $R_{12}$ contain as part of their structures a carboxylic acid ester group are disclosed in commonly owned U.S. Pat. Nos. 5,587,507 and 5,670,602, the disclosures of both of which are hereby incorporated by reference. The preferred desaminotyrosyl-tyrosine esters are the ethyl, butyl, hexyl, octyl and benzyl esters. For purposes of the present invention, desaminotyrosyl-tyrosine ethyl ester is referred to as DTE, desaminotyrosyl-tyrosine benzyl ester is referred to as DTBn, and the like. For purposes of the present invention, the non-ester desaminotyrosyl-tyrosine free carboxylic acid is referred to as DT.

It is not possible to polymerize the polycarbonates, polyarylates the poly(alkylene oxide) block copolymers thereof, having pendent free carboxylic acid groups from corresponding diphenols with pendent free carboxylic acid groups without cross-reaction of the free carboxylic acid group with the co-monomer. Accordingly, polycarbonates, polyarylates and the poly(alkylene oxide) block copolymers thereof that are homopolymers or copolymers of benzylester diphenol monomers such as DTBn may be converted to corresponding free carboxylic acid homopolymers and copolymers through the selective removal of the benzyl groups by the palladium catalyzed hydrogenolysis method disclosed by co-pending and commonly owned U.S. pat. application Ser. No. 09/056,050, filed on Apr. 7, 1998. The disclosure of this application is incorporated herein by reference. The catalytic hydrogenolysis is necessary because the ability of the polymer backbone prevents the employment of harsher hydrolysis techniques.

The bromine- and iodine-substituted dihydroxy compounds also include the aliphatic-aromatic dihydroxy compounds having the structure of Formula III in which $R_o$, $R_5$, $R_6$, $R_{15}$, $X_2$, Y2 and Z are the same as described above with respect to Formula III. Among the preferred aliphatic-aromatic dihydroxy compounds are compounds of Formula III in which $R_{15}$ is (—$CH_2$—)$_m$, wherein m is 0, Y2 is 1 and $R_5$ and $R_6$ are preferably independently selected from hydrogen and methyl. Z preferably has a structure according to Formula IV in which L is hydrogen or an ethyl, butyl, hexyl, octyl or benzyl group. L is more preferably hydrogen or an ethyl or benzyl group. When $R_5$ and $R_6$ are hydrogen, and $R_{15}$ (—$CH_2$—)$_m$, wherein m=0, the dihydroxy compound is derived from glycolic acid. When $R_{15}$ is the same, $R_5$ is hydrogen and $R_6$ is methyl, the dihydroxy compound is derived from lactic acid. Dihydroxy compounds derived from glycolic of lactic acid are particularly preferred.

Aliphatic-aromatic dihydroxy compounds that are not bromine- or iodine-substituted have the structure of Formula IIIc:

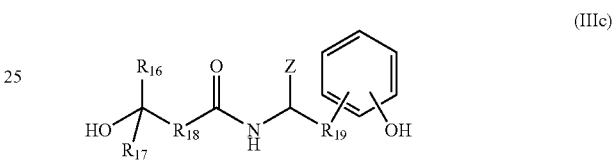

(IIIc)

wherein $R_{16}$, $R_{17}$, $R_{18}$, $R_{19}$, and Z are the same as described above with respect to Formula IIIb. Preferably, $R_{18}$ (—$CH_2$—)$_d$, in which d is 0 and $R_{16}$ and $R_{17}$ independently selected from hydrogen and methyl. Most preferably, one of $R_{16}$ and $R_{17}$ is hydrogen, while the other is methyl. The preferred species of Z are the same as described above with respect to Formula III.

The bromine- and iodine-substituted dihydroxy monomers of the present invention are prepared by well-known iodination and bromination techniques that can be readily employed by those of ordinary skill in the art without undue experimentation to prepare the monomer compounds depicted in Formulae I and III. The substituted phenols from which the dihydroxy monomers of the present invention are prepared undergo ortho-directed halogenation. For this reason, meta-iodinated and brominated dihydroxy monomers are not readily prepared, and triiodo- and tribromophenyl compounds have not been described. Such compounds are intended to be included within the scope of the present invention, should a convenient method for their synthesis be discovered.

Iodine- and bromine-substituted diphenol monomers may be prepared, for example, by coupling together two phenol compounds in which either or both of the phenol rings are iodine- or bromine-substituted. More specifically, desaminotyrosyl-tyrosine esters may be prepared by the methods described in the above-incorporated U.S. Pat. Nos. 5,587,507 and 5,670,602 using desaminotyrosine and tyrosine alkyl esters in which either or both compounds are bromine- or iodine-substituted. In a particularly preferred embodiment, desaminotyrosine is mono-iodinated at the ortho position on the phenolic ring and subsequently coupled with a tyrosine alkyl ester to obtain an iodine-substituted diphenol monomer.

Iodine- and bromine-substituted aliphatic-aromatic dihydroxy monomers in accordance with the present invention are prepared by coupling an α-, β- or γ-hydroxy acid with a phenolic compound in which either or both of the hydroxy acid and the diphenol are iodine- or bromine-substituted. For example, a tyrosine alkyl ester is mono-iodinated at the ortho position on the phenolic ring and subsequently coupled with an α-, β- or γ-hydroxy acid according to the method described in the above-incorporated International Publication 98/36013 to obtain an iodine-substituted aliphatic-aromatic dihydroxy monomer.

Polycarbonates, polyarylates, poly(alkylene oxide) block copolymers thereof having pendent free carboxylic acid groups also cannot be polymerized from an aliphatic-aromatic dihydroxy monomer having a pendent free carboxylic acid group because of cross-reaction with the co-monomer. Methods for preparing the aliphatic-aromatic dihydroxy monomers of Formulae III and IIIc in which L of Z is not hydrogen are disclosed in commonly owned International Publication No. 98/36013, the disclosure of which is hereby incorporated by reference. L of Z is preferably an ethyl, butyl, hexyl, octyl or benzyl group. Polycarbonates, polyarylates and the poly(alkylene oxide) block copolymers thereof having pendent free carboxylic acid groups can also be prepared by the palladium-catalyzed hydrogenolysis of the corresponding polymers with benzyl esters prepared as described in the earlier-referenced U.S. patent application Ser. No. 09/056,050. The catalytic hydrogenolysis may be performed as described in this Provisional Patent Application, as well.

Polyarylates and polycarbonates, alone, or as segments within a poly(alkylene oxide) block copolymer, may be homopolymers with each dihydroxy monomeric subunit having an iodine or a bromine atom. The polymers of the present invention also include copolymers of the same polymer units with dihydroxy monomers that are iodine- and bromine-free. One can vary within the polymers the molar ratios of the monomeric subunits having bromine- and iodine atoms and the monomeric subunits that are bromine- and iodine-free.

Polymers in accordance with the present invention thus include homopolymers of a repeating unit having at least one iodine or bromine atom. Such homopolymers have the structure of Formulae VIII and VIIIa in which f and g are both zero.

Polymers in accordance with the present invention thus also include copolymers having monomeric repeating units that are bromine- and iodine-free. Such copolymers have the structure of Formulae VIII or VIIIa in which f is zero and g is a number greater than zero but less than one. In copolymers in accordance with the present invention, g is preferably between about 0.25 and about 0.75.

In the preferred homopolymers and copolymers of Formula VIII, $R_9$ has the structure of Formula II and $R_{12}$ has the structure of Formula V. The preferred species thereof are the same as described above with respect to Formula II and Formula V.

When A of Formulae VIII and VIIIa is:

the polymers of the present invention are polycarbonates. When f is zero, the iodine- and bromine-substituted polycarbonate homopolymers and copolymers of the present invention may be prepared by the method described by U.S. Pat. No. 5,099,060 and by U.S. patent application Ser. No. 08/884,108, filed Jun. 27, 1997, the disclosures of both of which are also incorporated herein by reference. The described method is essentially the conventional method for polymerizing dihydroxy monomers into polycarbonates. Suitable processes, associated catalysts and solvents are known in the art and are taught in Schnell, *Chemistry and Physics of Polycarbonates*, (Interscience, New York 1964), the teachings of which are incorporated herein by reference.

The polycarbonate homopolymers and copolymers in accordance with the present invention in which f=0 have weight-average molecular weights ranging between about 20,000 to about 400,000 daltons, and preferably about 100,000 daltons, measured by gel permeation chromatography (GPC) relative to polystyrene standards without further correction.

When A of Formulae VIII and VIIIa is:

 (X)

the polymers of the present invention are polyarylates. The iodine- and bromine-substituted polyarylate homopolymers and copolymers of the present invention may be prepared by the method described by U.S. Pat. No. 5,216,115, in which dihydroxy monomers are reacted with aliphatic or aromatic dicarboxylic acids in a carbodiimide mediated direct polyesterification using 4-(dimethylamino)pyridinium-p-toluene sulfonate (DPTS) as a catalyst to form aliphatic or aromatic polyarylates. The disclosure of this patent is also incorporated herein by reference. It should be noted that $R_8$ should not be substituted with functional groups that would cross-react.

Dicarboxylic acids from which the polyarylates materials of the present invention may be polymerized have the structure of Formula X:

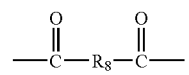

in which, for the aliphatic polyarylates, $R_8$ is selected from saturated and unsaturated, substituted and unsubstituted alkyl groups containing up to 18 carbon atoms, and preferably from 4 to 12 carbon atoms. For aromatic polyarylates, $R_8$ is selected from aryl and alkylaryl groups containing up to 18 carbon atoms, but preferably from 8 to 14 carbon atoms. Again, $R_8$ should not be substituted with functional groups that would cross-react.

$R_8$ is even more preferably selected so that the dicarboxylic acids from which the polyarylate starting materials are polymerized are either important naturally-occurring metabolites or highly biocompatible compounds. Preferred aliphatic dicarboxylic acids therefore include the intermediate dicarboxylic acids of the cellular respiration pathway known as the Krebs Cycle. These dicarboxylic acids include alpha-ketoglutaric acid, succinic acid, fumaric acid, maleic acid and oxalacetic acid. Other preferred biocompatible aliphatic dicarboxylic acids include sebacic acid, adipic acid, oxalic acid, malonic acid, glutaric acid, pimelic acid, suberic acid and azelaic acid. Among the preferred aromatic dicarboxylic acids are terephthalic acid, isophthalic acid and bis(p-carboxyphenoxy)alkanes such as bis(p-carboxyphenoxy)propane. Stated another way, $R_8$ is more preferably a moiety selected from —$CH_2$—C(=O)—, —$CH_2$—$CH_2$—C(=O)—, —CH=CH— and (—$CH_2$—)$_z$, wherein z is an integer between two and eight, inclusive.

Iodine- and bromine-substituted polyarylate homopolymers and copolymers in accordance with the present invention have weight average molecular weights between about 20,000 and about 400,000 daltons, and preferably about 100,000 daltons, measured by GPC relative to polystyrene standards without further correction.

Iodine- and bromine-substituted polycarbonates and polyarylates in accordance with the present invention also include random block copolymers with a poly(alkylene oxide) with the structure of Formulae VIII or VIIIa, wherein f is greater than zero but less than one. The variable species, and the preferred embodiments thereof, are the same as described above with respect to formulae VIII and VIIIa, except that f is no longer zero and the value for g is less than one, and g may or may not be greater than zero.

The molar fraction of alkylene oxide in the block copolymer, f, ranges between about 0.01 and about 0.99. For preferred block copolymers, $R_7$ is ethylene, k is between about 20 and about 200, and the molar fraction of alkylene oxide in the block copolymer, f, preferably ranges between about 0.05 and about 0.75. $R_7$ may also represent two or more different alkylene groups within a polymer.

The block copolymers of the present invention may be prepared by the method described by U.S. Pat. No. 5,658,995, the disclosure of which is also incorporated herein by reference. The block copolymers have weight-average molecular weights between about 20,000 and about 400,000 daltons, and preferably about 100,000 daltons. The number-average molecular weights of the block copolymers are preferably above about 50,000 daltons. Molecular weight determinations are measured by GPC relative to PEG standards without further correction.

For homopolymers and copolymers in accordance with the present invention having pendent carboxylic acid amide or ester groups, the amide or ester group can be an amide or ester derivative of a biologically or pharmaceutically active compound covalently thereto. The covalent bond is by means of an amide bond when in the underivatized biologically or pharmaceutically active compound a primary or secondary amine is present at the position of the amide bond in the derivative. The covalent bond is by means of an ester bond when in the underivatized biologically or pharmaceutically active compound a primary hydroxyl is present at the position of the ester bond in the derivative. The biologically or pharmaceutically active compounds may also be derivatized at a ketone, aldehyde or carboxylic acid group with a linkage moiety such as the linkage moiety $R_3$ of Formula IIIa, which is covalently bonded to the copolymer or diphenol by means of an amide or ester bond.

Detailed chemical procedures for the attachment of various drugs and ligands to polymer bound free carboxylic acid groups have been described in the literature. See, for example, U.S. Pat. Nos 5,219,564 and 5,660,822; Nathan et al, *Bio. Cong. Chem.*, 4, 54–62 (1993) and Nathan, *Macromolecules*, 25, 44–76 (1992). The disclosures of both patents in both journal articles are incorporated herein by reference. These publications disclose procedures by which polymers having pendent free carboxylic acid group are reacted with moieties having reactive functional groups, or that are derivatized to contain active functional groups to form a polymer conjugate.

The order of reaction can also be reversed. The moiety may first be attached to a monomer having a pendent free carboxylic acid group, which is then polymerized to form a polymer in which 100% of the pendent free carboxylic acid groups have moieties attached thereto.

When a polymer having pendent free carboxylic acid groups is first polymerized and then reacted with a biologically or pharmaceutically active compound or derivative thereof to form a polymer conjugate not all of the pendent free carboxylic acid groups will have a biologically or pharmaceutically active compound covalently attached thereto. Typically, a conjugate is formed in which biologically or pharmaceutically active compounds attach to at least about 25% of the pendent free carboxylic acid groups.

Examples of biologically or pharmaceutically active compounds suitable for use with the present invention include acyclovir, cephradine, malphalen, procaine, ephedrine, adriamycin, daunomycin, plumbagin, atropine, quinine, digoxin, quinidine, biologically active peptides, chlorin $e_6$, cephradine, cephalothin, proline and proline analogs such as cis-hydroxy-L-proline, melphalan, penicillin V, aspirin, nicotinic acid, chemodeoxycholic acid, chlorambucil, and the like. Biologically active compounds, for purposes of the present invention are additionally defined as including cell attachment mediators, biologically active ligand and the like. The compounds are covalently bonded to the polycarbonate or polyarylate copolymer by methods well understood by those of ordinary skill in the art. Drug delivery compounds may also be formed by physically blending the biologically or pharmaceutically active compound to be delivered with the polymers of the present invention. Either way, the polymers of the present invention provide a means by which drug delivery may be monitored using x-ray imaging without having to employ a filler material to provide x-ray contrast.

For purposes of the present invention, the alkyl ester and amide groups within Z are also defined as including crosslinking moieties, such as molecules with double bonds (e.g., acrylic acid derivatives), which can be attached to the pendent carboxylic acid groups for crosslinking to increase the strength of the polymers.

As noted above, the polymers of the present invention are iodine or bromine substituted at selected repeating subunits. For the purposes of the present invention, homopolymers (Formula VIII or VIIIa, x=0) are defined as containing an iodine or bromine at each subunit. These homopolymers can be polycarbonates or polyarylates which may contain polyalkylene oxide blocks. The homopolymers are best described as new, radio-opaque polymers that may have a number of pharmacological and biological activities. Likewise, for the purposes of the present invention, copolymers (Formula VIII or VIIIa, 0<x<1) are defined as containing iodine or bromine at some of the diphenolic subunits. These copolymers can be polycarbonates or polyarylates, which also may contain polyalkylene oxide blocks.

The invention described herein also includes various pharmaceutical dosage forms containing the polymers of the present invention. The pharmaceutical dosage forms include those recognized conventionally, e.g. tablets, capsules, oral liquids and solutions, drops, parenteral solutions and suspensions, emulsions, oral powders, inhalable solutions or powders, aerosols, topical solutions, suspensions, emulsions, creams, lotions, ointments, transdermal liquids and the like.

The pharmaceutical dosage forms may include one or more pharmaceutically acceptable carriers. Such materials are non-toxic to the recipients at the dosages and concentrations employed, and include diluents, solubilizers, lubricants, suspending agents, encapsulating materials, penetration enhancers, solvents, emollients, thickeners, dispersants, buffers such as phosphate, citrate, acetate and other organic acid salts, anti-oxidants such as ascorbic acid, preservatives, low molecular weight (less than about 10 residues) peptides such as polyarginine, proteins such as serum albumin, gelatin, or immunoglobulins, other hydrophilic polymers such as poly(vinylpyrrolidinone), amino acids such as glycine, glutamic acid, aspartic acid, or arginine, monosaccharides, disaccharides, and other carbohydrates, including cellulose or its derivatives, glucose, mannose, or dextrines, chelating agents such as EDTA, sugar alcohols such as mannitol or sorbitol, counterions such as sodium and/or nonionic surfactants such as tween, pluronics or PEG.

The drug-polymer compositions of the present invention, regardless of whether they are in the form of polymer-drug conjugates or physical admixtures of polymer and drug, are suitable for applications where localized drug delivery is desired, as well as in situations where a systemic delivery is desired. The polymer-drug conjugates and physical admixtures may be implanted in the body of a patient in need thereof, by procedures that are essentially conventional and well-known to those of ordinary skill in the art.

Hydrolytically stable conjugates are utilized when the biological or pharmaceutical compound is active in conjugated form. Hydrolyzable conjugates are utilized when the biological or pharmaceutical compound is inactive in conjugated form. The properties of the poly(alkylene oxide) dominate the polymer and conjugate thereof.

Conjugates of the polymers of the present invention with proline and proline analogs such as cis-hydroxy-L-proline may be used in the treatment methods disclosed in U.S. Pat. No. 5,660,822. The disclosure of this patent is incorporated herein by reference.

Physical admixtures of drug and polymer are prepared using conventional techniques well-known to those of ordinary skill in the art. For this drug delivery embodiment, it is not essential that the polymer have pendent free carboxylic acid groups.

The drug components to be incorporated in the polymer-drug conjugates and physical admixtures of this invention may be provided in a physiologically acceptable carrier, excipient stabilizer, etc., and may be provided in sustained release or timed release formulations supplemental to the polymeric formulation prepared in this invention. The carriers and diluents listed above for aqueous dispersions are also suitable for use with the polymer-drug conjugates and physical admixtures.

Subjects in need of treatment, typically mammalian, using the polymer-drug combinations of this invention, can be administered drug dosages that will provide optimal efficacy. The dose and method of administration will vary from subject to subject and be dependent upon such factors as the type of mammal being treated, its sex, weight, diet, concurrent medication, overall clinical condition, the particular compounds employed, the specific use for which these compounds are employed, and other factors which those skilled in the medical arts will recognize. The polymer-drug combinations of this invention may be prepared for storage under conditions suitable for the preservation of drug activity as well as maintaining the integrity of the polymers, and are typically suitable for storage at ambient or refrigerated temperatures.

Aerosol preparations are typically suitable for nasal or oral inhalation, and may be in powder or solution form, in combination with a compressed gas, typically compressed air. Additionally, aerosols may be used topically. In general, topical preparations may be formulated to enable one to apply the appropriate dosage to the affected area once daily, and up to three to four times daily, as appropriate.

Depending upon the particular compound selected, transdermal delivery may be an option, providing a relatively steady delivery of the drug, which is preferred in some circumstances. Transdermal delivery typically involves the use of a compound in solution, with an alcoholic vehicle, optionally a penetration enhancer, such as a surfactant, and other optional ingredients. Matrix and reservoir type transdermal delivery systems are examples of suitable transdermal systems. Transdermal delivery differs from conventional topical treatment in that the dosage form delivers a systemic dose of the drug to the patient.

The polymer-drug formulations of this invention may also be administered in the form of liposome delivery systems, such as small unilamellar vesicles, large unilamellar vesicles and multilamellar vesicles. Liposomes may be used in any of the appropriate routes of administration described herein. For example, liposomes may be formulated that can be administered orally, parenterally, transdermally, or via inhalation. Drug toxicity could thus be reduced by selective drug delivery to the affected site. For example, if the drug is liposome encapsulated, and is injected intravenously, the liposomes used are taken up by vascular cells and locally high concentrations of the drug could be released over time within the blood vessel wall, resulting in improved drug action. The liposome encapsulated drugs are preferably administered parenterally, and particularly, by intravenous injection.

Liposomes may be targeted to a particular site for drug release. This would obviate excessive dosages that are often necessary to provide a therapeutically useful dosage of a drug at the site of activity, and consequently, the toxicity and side effects associated with higher dosages.

The drugs incorporated into the polymers of this invention may desirably further incorporate agents to facilitate their delivery systemically to the desired drug target, as long as the delivery agent meets the same eligibility criteria as the drugs described above. The active drugs to be delivered may in this fashion be incorporated with antibodies, antibody fragments, growth factors, hormones, or other targeting moieties, to which the drug molecules are coupled. The polymer-drug combinations of this invention may be formed into shaped particles, such as valves, stents, tubing, prostheses, and the like.

Therapeutically effective dosages may be determined by either in vitro or in vivo methods. For each particular compound of the present invention, individual determinations may be made to determine the optimal dosage required. The range of therapeutically effective dosages will naturally be influenced by the route of administration, the therapeutic objectives, and the condition of the patient. For the various suitable routes of administration, the absorption efficiency must be individually determined for each drug by methods well known in pharmacology. Accordingly, it may be necessary for the therapist to titer the dosage and modify the route of administration as required to obtain the optimal therapeutic effect. The determination of effective dosage levels, that is, the dosage levels necessary to achieve the desired result, will be within the ambit of one skilled in the art. Typically, applications of compound are commenced at lower dosage levels, with dosage levels being increased until the desired effect is achieved. The release rate of the drug from the formulations of this invention are also varied within the routine skill in the art to determine an advantageous profile, depending on the therapeutic conditions to be treated.

A typical dosage might range from about 0.001 mg/k/g to about 1,000 mg/k/g, preferably from about 0.01 mg/k/g to about 100 mg/k/g, and more preferably from about 0.10 mg/k/g to about 20 mg/k/g. Advantageously, the compounds of this invention may be administered several times daily, and other dosage regimens may also be useful.

In practicing the methods of this invention, the polymer-drug combinations may be used alone or in combination with other therapeutic or diagnostic agents. The compounds of this invention can be utilized in vivo, ordinarily in mammals such as primates such as humans, sheep, horses, cattle, pigs, dogs, cats, rats and mice, or in vitro.

The polymers of the present invention also find application in areas where both solid materials and solvent-soluble materials are commonly employed. Such applications include polymeric scaffolds in tissue engineering applications and medical implant applications, including the use of the polymers of the present invention to form shaped articles such as vascular grafts and stents, bone plates, sutures, implantable sensors, scaffolds for tissue regeneration, and other therapeutic agent particles that decompose harmlessly within a known period of time. Shaped particles can be formed by conventional techniques such as extrusion, compression molding, injection molding, solvent casting, spin casting, and the like.

The polymers of the present invention are soluble in both water and organic media. Accordingly, they can be processed by solvent casting techniques and are good film formers. The polymers of the present invention having pendent free carboxylic acid groups can also be used to influence the interactions with cells, as disclosed in the above-referenced International Publication No. 98/36013.

The incorporation of polyalkylene oxide blocks decreases the adhesiveness of the polymeric surfaces. Polymers for which f is greater than 5 mole percent according to Formulae VIII or VIIIa are resistant to cell attachment and may be useful as non-thrombogenic coatings on surfaces in contact with blood. These polymers also resist bacterial adhesion. The polymers thus can be formed as a coating on the surface of medical devices by conventional dipping or spray coating techniques to prevent the formation of blood clots or the adhesion of bacteria on the surface of the device.

The film forming properties of polymers with poly(alkylene oxide) can be advantageously combined with the resistance to cell attachment to provide films for use as barriers for the prevention of surgical adhesions. A coating of the polymer of the present invention may also be applied to injured tissue to provide a surgical adhesion barrier.

The polymers of the present invention can find application in areas where both structural solid materials and water-soluble materials are commonly employed. Such applications include polymeric scaffolds in tissue engineering applications and medical implant applications, including the use of the polycarbonates and polyarylates of the present invention to form shaped articles such as vascular grafts and stents, bone plates, sutures, implantable sensors, barriers for surgical adhesion prevention, implantable drug delivery devices, scaffolds for tissue regeneration, and other therapeutic agent articles that decompose harmlessly within a known period of time.

INDUSTRIAL APPLICABILITY

Shaped articles may be prepared from the polymers of the present invention for medical implant and drug delivery applications. The articles are radio-opaque and may be monitored using x-ray imaging without having to employ a filler material to provide x-ray contrast.

The following non-limiting examples set forth hereinbelow illustrate certain aspects of the invention. All parts and percentages are by mole percent unless otherwise noted and all temperatures are in degrees Celsius. All solvents were HPLC grade. All other reagents were of analytical grade and were used as received.

The following Examples illustrate the preparation of 3-(3-iodo-4-hydroxyphenyl)propanoic acid-tyrosine ethyl ester (DiTE), and its incorporation into a variety of polymer structures. Since an iodine is present is the structure of DiTE, the materials illustrated in the following Examples are radio-opaque.

EXAMPLE 1

Synthesis of DiTE

DiTE (3-(3-iodo-4-hydroxyphenyl)propanoic acid-tyrosine ethyl ester) is a bisphenol carrying one iodine atom at position 3 of one of the two phenolic rings. This bifunctional molecule can be polymerized as illustrated in the subsequent Examples. This Example describes the method used to introduce the iodine atom in the aromatic ring (4-hydroxyphenyl)propionic acid, and the coupling of this iodinated derivative with tyrosine ethyl ester in order to obtain DiTE.

Preparation of solution (a): to a 250 mL Erlenmeyer flask were added 100 mL of distilled water, 24 g of potassium iodide, and 25 g of iodine. The mixture was stirred overnight until all solids dissolved.

Preparation of solution (b): 16.6 g (0.1 mole) of DAT were placed in a 3-necked Morton-type round bottom flask, equipped with an overhead mixer and a 125 mL addition funnel. 140 mL of 40% trimethylamine solution in water were added, and the mixture was stirred until a clear solution was obtained.

Solution (a) was placed in the addition funnel, and added dropwise to solution (b) while vigorously stirring. Addition of each drop of solution (a) imparted a brown color to the reaction mixture. The rate of addition was such that all the color disappeared before the next drop was added. Stirring was continued for one hour after the last addition, the 50 mL of sodium thiosulfate 0.1 M were added to the reaction vessel. The same solution was also used to wash the addition funnel.

37% HCl was added dropwise with vigorous mixing until the solution was slightly acidic to litmus, and a solid formed. The mixture was concentrated to half its volume by rotary evaporation, and then it was extracted with ether. The organic phase was dried over magnesium sulfate, and decolorized using animal charcoal. The slurry was then filtered through a small layer of silica gel, and evaporated to dryness. The white solid was recrystallized twice in toluene, recovered by filtration, dried under a stream of nitrogen, and then under high vacuum.

Characterization: DSC analysis showed a melting point range of 109–111° C. $^1$H-NMR (DMSO) of the product showed the following peaks (ppm): 2.5 (t, 2H), 2.7 (t, 2H), 6.8 (d, 2H), 7.06 (d, 2H), 10.08 (s, 1H), 12.05 (s, 1H). Reverse-phase HPL showed 3.8% DAT (the starting material), and 1.4% of diiodinated product.

Step 2: Preparation of 3-(3-iodo-4-hydroxyphenyl)propionic Acid-tyrosine Ethyl Ester (DiTE)

To a 250 mL 3-necked round bottomed flask equipped with an overhead stirrer were added 17.0 g (0.0582 moles) of DiAT, 12.25 g (0.0585 moles) or tyrosine ethyl ester, and 25 mL of NMP. The mixture was stirred until a clear solution was obtained. The flask was cooled in an ice-water bath, the 11.84 g (0.0619 moles) of EDCI HCl were added in one portion, followed by 15 mL of NMP. The cooling bath was removed after 2.5 hours, and the reaction was allowed to continue overnight at room temperature. 71 mL of ethyl acetate were added, and stirring was maintained for 15 more minutes. The crude was then transferred into a 500 mL separatory funnel, and extracted once with 75 mL of brine, then with two aliquots (75 and 35 mL) of 3% NaHCO3/14% NaCl, followed by 35 mL aliquots of 0.4M HCl/14% NaCl, and finally with brine. The organic phase was dried over magnesium sulfate and treated with activated carbon, filtered and concentrated to a thick syrup, which crystallized into a solid mass after a few hours. The product was triturated in methylene chloride using mechanical stirring, then it was recovered by filtration and dried under a nitrogen stream followed by high vacuum.

Characterization: DSC analysis showed a melting point range of 110–113° C. $_1$H-NMR (DMSO) showed the following peaks (ppm): 1.1 (t, 3H), 2.35 (t, 2H), 2.65 (m, 2H), 2.85 (m, 2H), 4.05 (q, 2H), 4.35 (m, 1H), 6.65/6.75/6.95 (m, 6H), 7.5 (s, 1H), 8.25 (d, 1H), 9.25 (s, 1H), 10.05 (s, 1H). Reverse-phase HPLC showed 2.2% of DTE (the non-iodinated monomer), and no diiodinated product.

EXAMPLE 2

Poly(DiTE Carbonate) by Solution Polymerization

This material is the polycarbonate obtained by reacting DiTE, obtained in Example 1, and phosgene.

Polymerization of DiTE with Phosgene

A 250 mL 3-necked flask equipped with a mechanical stirrer and an addition funnel was purged with nitrogen for 15 minutes. 7.62 g (15.8 moles) of DiTE were added to the flask followed by 39 mL methylene chloride and 4.79 mL distilled pyridine. The mixture was stirred until a clear solution was obtained, then it was chilled in an ice-water bath. 9.8 mL of 20% phosgene solution in toluene were placed in the addition funnel and added to the reaction flask at a constant rate so that the entire addition was complete in 1.5 hours. The mixture was stirred for one more hour, then it was diluted with 200 mL THF, and the polymer was precipitated by dropping the solution in a large excess of ether through a filter funnel. The precipitated polymer was washed with ether, transferred to an evaporating dish, and dried overnight under a steam of nitrogen. It was redissolved in THF, and precipitated again in a water/ice mixture, using a high-speed blender. The product was then dried under a stream of nitrogen, followed by high vacuum at 40° C.

Characterization: The composition of the product was confirmed by Elemental Analysis: % C=50.60 (theor: 49.52%); % H=4.21 (theor: 3.96%); % N=2.65 (theor: 2.75%); % I-24.01 (theor: 24.92%). A Mw of 104K with a polydispersity of 1.8 was determined by GPC in THF vs. polystyrene standards. DSC showed a Tg of 103.8° C. $^1$H-NMR (DMSO-D$_6$) showed the following peaks (ppm): 1.1. (t, 3), 2.4 (broad, 2H), 2.75 (broad, 2H), 3.0 (broad, 2H), 4.05 (q, 2), 4.45 (m, 1H), 7.3 (m, 6H), 7.8 (s, 1H), 8.4 (d, 1H).

EXAMPLE 3

Poly(DiTE-co-5% PEG1K Carbonate) by Solution Polymerization

In this Example, 5 mole % of PEG1000 was copolymerized with DiTE through phosgenation by means of a solution polymerization technique similar to that described in Example 2. The resulting material is a random polycarbonate.

Copolymerization of DiTE and PEG1000

A 100 mL 3-necked round bottomed flask equipped with an addition funnel and an overhead stirrer was purged with nitrogen for 30 minutes. The flask was charged with 5 g (10.33 mmoles) of DiTE, and 0.545 g (0.55 mmoles) of PEG1000, then 23 mL of methylene chloride and 3.3 mL of pyridine were added, and the mixture was stirred until a colorless, clear solution resulted. The flask was cooled in an ice-water bath, and 6.4 mL of 20% phosgene solution in toluene were added dropwise over a period of 90 minutes from the addition funnel. The mixture was diluted with 90 mL of THE, and stirred for one more hour. The product was isolated by precipitation in 800 mL of ethyl ether, and dried under a stream of nitrogen followed by high vacuum.

Characterization: A Mw of 75,500 with a polydispersity of 1.8 was determined by GPC vs. polystyrene standards, with THF as the mobile phase. DSC showed Tg of 70° C. $^1$H-NMR (CDCl$_3$) showed the following peaks (ppm): 1.2 (t, 3H), 2.45 (broad, 2H), 2.8 (broad, 2H), 2.03 (broad, 2H), 3.65 (s, 4.5 PEG protons), 4.15 (q, 2H), 4.85 (m, 1H), 6.05 (broad, 1H), 7.05/7.15 (m, 6H), 7.2 (s, 1H). The peaks at 7.05/7.15, and at 7.2 are diagnostic for the presence of the iodine atom on the aromatic system of the polymer. Broad-Band Decoupled $^{13}$C NMR (CDCl$_3$) showed all the expected peaks, and in particular that of the aromatic carbon bearing the iodine (90 ppm).

EXAMPLE 4

Poly(DiTE Adipate) by Solution Polymerization

This material is an alternating copolymer of the iodine-containing diphenol DiTE, and adipic acid, an aliphatic diacid. The monomers are linked through an ester bond to form a polyarylate backbone. This Example illustrates the preparation of this copolymer by means of a condensation reaction promoted by the coupling agent diisopropylcarbodiimide (DIPC).

Copolymerization of DiTE and Adipic Acid

A 100 mL round bottomed flask equipped with an overhead stirrer was purged with nitrogen for one hour, and then charged with 4.349 g (9.0 mmoles) of DiTE, 1.315 g (9.0 mmoles) of adipic acid, 1.06 of dimethylaminopyridinium p-toluene sulfonate (2.5 mmoles), and 68 mL of methylene chloride. The mixture was stirred for five minutes, then 4.2 mL (27 mmoles) of DIPC were added in one portion. Stirring was continued overnight at room temperature, then the reaction crude was filtered, and the polymer was precipitated in 600 mL of chilled isopropanol in a high-speed blender, and isolated by filtration. The polymer was washed in the high-speed blender with 600 mL of chilled isopropanol, and the 600 mL of a water/ice mixture. The product was dried overnight under a stream of nitrogen, and then was transferred to high vacuum at room temperature.

Characterization: A Mw of 67,100 with a polydispersity of 1.9 was determined by GPC vs. polystyrene standards, with THF as the mobile phase. DSC showed a Tg of 66.5° C. ¹H-NMR (DMSO-D$_6$) showed the following peaks (ppm): 1.1 (t, 3H), 1.75 (broad, 4H), 2.4 (broad, 2H), 2.7 (broad, 6H), 2.95 (broad, 2H),.4.05 (q, 2H0, 4.45 (m, 1H), 7.05/7.15 (m, 6H), 7.7 (s, 1H), 8.4 (d, 1H).

EXAMPLE 6

Fabrication and Implantation of Radio-Opaque Rods

Iodine-containing, radio-opaque polymers can be blended with nonradio-opaque materials in order to fabricate implantable devices that are x-ray detectable. This example illustrates the preparation of blends of poly(DTE carbonate) and poly(DiTE carbonate) in three different ratios, their fabrication into rods, and their implantation into an animal model.

Preparation of Radio-opaque Polymer Blends

Three blends with different ratios of poly(DTE carbonate) (Mw=103 K) to poly(DiTE carbonate) (Mw=106 K) were prepared. The weight ratios were 90/10, 75/25 and 50/50. In each case, the polymers were co-dissolved in methylene chloride, and the mixture was precipitated in ether.

Fabrication and Implantation of Radio-opaque Rods

Uniform rods of 10 mm length, 2 mm diameter were obtained by melt extrusion at 180° C. The rods were implanted in rabbit long bones, and sites of implantation were x-rayed in order to confirm the radio-opacity of the devices. Radio-opacity increased with increasing content of poly(DiTE carbonate).

The foregoing examples illustrate that radio opacity may be obtained by Br and I ring-substitution of essentially any aromatic ring-containing polymer. These examples, and the foregoing description of the preferred embodiment, should be taken as illustrating, rather than as limiting, the present invention as defined by the claims. As will be readily appreciated, numerous variations and combinations of the features set forth above can be utilized without departing from the present invention as set forth in the claims. Such variations are not regarded as a departure from the spirit and scope of the invention, and all such modifications are intended to be included within the scope of the following claims.

What is claimed is:

1. An implantable, radio-opaque medical device comprising a radio-opaque, iodine- or bromine-substituted polymer described by the formula VIII:

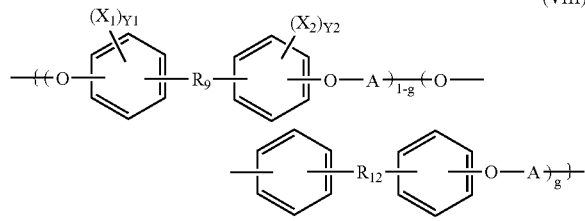

(VIII)

wherein X$_1$ and X$_2$ are independently I or Br; Y1 and Y2 are independently 0,1, or 2; R$_9$ and R$_{12}$ are independently an alkyl, aryl, or alkylaryl group containing up to 18 carbon atoms; A is:

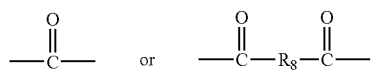

wherein R$_8$ is selected from the group consisting of saturated and unsaturated, substituted and unsubstituted alkyl, aryl, and alkylaryl groups containing up to 18 carbon atoms; R$_8$, R$_9$, or R$_{12}$ is optionally bromine- or iodine-substituted; and g is between 0 and 0.99, inclusive.

2. The implantable, radio-opaque medical device of claim 1 wherein g is zero.

3. The implantable, radio-opaque medical device of claim 1 wherein R$_9$ has the structure:

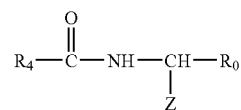

wherein R$_0$ is selected from the group consisting of —CH═CH—, —CHJ$_1$-CHJ$_2$-, and (—CH$_2$—)$_m$, R$_4$ is selected from the group consisting of —CH═CH—, —CHJ$_1$-CHJ$_2$-, and (—CH$_2$—)$_a$, wherein m and a are independently between 0 and 8, inclusive; J$_1$ and J$_2$ are independently Br or I; and Z is selected from the group consisting of hydrogen, a free carboxylic acid group, and carboxylic acid esters and amides, wherein said ester and amides are selected from the group consisting of esters and amides of straight and branched alkyl and alkyaryl groups containing up to 18 carbon atoms and esters and amides of biologically and pharmaceutically active compounds.

4. The implantable, radio-opaque medical device of claim 3 wherein g is greater than zero and R$_{12}$ has the structure:

$$R_4-\overset{O}{\underset{\|}{C}}-NH-\underset{Z}{\overset{|}{C}H}-R_0$$

wherein R$_0$ is selected from the group consisting of —CH═CH—, —CHJ$_1$-CHJ$_2$-, and (—CH$_2$—)m, R$_4$ is selected from the group consisting of —CH═CH—, —CHJ$_1$-CHJ$_2$-, and (—CH$_2$—)$_a$, wherein m and a are independently between 0 and 8, inclusive; J$_1$ and J$_2$ are independently Br or I; and Z is selected from the group consisting of hydrogen, a free carboxylic acid group, and carboxylic acid esters and amides, wherein said ester and amides are selected from the group consisting of esters and amides of straight and branched alkyl and alkyaryl groups containing up to 18 carbon atoms and esters and amides of biologically and pharmaceutically active compounds.

5. The implantable, radio-opaque medical device of claim 4 wherein R$_9$ has the structure:

$$-(CH_2)_c-\overset{O}{\underset{\|}{C}}-NH-\underset{Z}{\overset{|}{C}H}-(CH_2)_d-$$

and R$_{12}$ has the structure:

$$-(CH_2)_a-\overset{O}{\underset{\|}{C}}-NH-\underset{Z}{\overset{|}{C}H}-(CH_2)_b-$$

wherein a and c are two and b and d are one.

6. The implantable, radio-opaque medical device of claim 4 wherein each Z of R$_9$ and R$_{12}$ is an ester of a carboxylic acid; wherein each ester group is independently selected from the group consisting of ethyl, butyl, hexyl, octyl, and benzyl groups.

7. The implantable, radio-opaque medical device of claim 1 wherein A is:

$$-\overset{O}{\underset{\|}{C}}-.$$

8. The implantable, radio-opaque medical device of claim 1 wherein A is:

$$-\overset{O}{\underset{\|}{C}}-R_8-\overset{O}{\underset{\|}{C}}-.$$

9. The implantable, radio-opaque medical device of claim 8 wherein $R_8$ is selected from the group consisting of saturated and unsaturated, substituted and unsubstituted alkyl groups containing up to 8 carbon atoms.

10. The implantable, radio-opaque medical device of claim 9 wherein $R_8$ is selected from the group consisting of —$CH_2$—C(=O)—, —$CH_2CH_2$—C(=O)—, CH=CH—, and (—$CH_2$—)$_Q$, wherein Q is between 0 and 8, inclusive.

11. The implantable, radio-opaque medical device of claim 8 wherein $R_8$ is selected from the group consisting of saturated and unsaturated, substituted and unsubstituted aryl and alkyaryl groups containing from 13 to 20 carbon atoms.

12. The implantable, radio-opaque medical device of claim 8 wherein $Y_1+Y_2$ is greater than zero.

13. The implantable, radio-opaque medical device of claim 1 wherein said polymer further comprises one or more poly(alkylene oxide) blocks.

14. The implantable, radio-opaque medical device of claim 1 wherein said medical device is formed from said polymer.

15. The implantable, radio-opaque medical device of claim 1 wherein said medical device is coated with said polymer.

16. The implantable, radio-opaque medical device of claim 1 wherein said device comprises a radio-opaque, biocompatible stent comprising said polymer.

17. The implantable, radio-opaque medical device of claim 14 wherein said device is a radio-opaque, biocompatible stent.

18. An implantable, radio-opaque medical device comprising a radio-opaque, iodine- or bromine-substituted polymer described by the formula VIIIa:

(b) $R_{15}$ is selected from the group consisting of (—$CH_2$—)$_c$, —CH=CH—, and —$CJ_1$-$CJ_2$-, wherein -$J_1$ and $J_2$ are independently Br or I and c is between 0 and 8, inclusive;

(c) X2 is Br or I, and Y2 is 0, 1 or 2;

(d) Z is selected from the group consisting of hydrogen, a free carboxylic acid group or an ester or amide thereof;

(e) A is:

$$-\overset{O}{\underset{\|}{C}}- \quad \text{or} \quad -\overset{O}{\underset{\|}{C}}-R_8-\overset{O}{\underset{\|}{C}}-$$

wherein $R_8$ is selected from the group consisting of saturated and unsaturated, substituted and unsubstituted alkyl, aryl, and alkylaryl groups containing up to 18 carbon atoms;

(f) each $R_0$ is independently —CH=CH— or (—$CH_2$—)$_d$, wherein d is between 0 and 8 inclusive; and (g) g is greater than zero but less than one.

19. The implantable, radio-opaque medical device of claim 18 wherein $R_0$ or $R_{15}$ are (—$CH_2$—)$_d$ or (—$CH_2$—)$_c$, respectively, wherein c or d are 0, and $R_5$, $R_6$, $R_{16}$, and $R_{17}$ are independently hydrogen or a methyl group.

20. The implantable, radio-opaque medical device of claim 19 wherein $R_5$, $R_6$, $R_{16}$, and $R_{17}$ are all hydrogen.

21. The implantable, radio-opaque medical device of claim 19 wherein one of $R_5$ and $R_6$ or $R_{16}$ and $R_{17}$ is hydrogen and the others are methyl.

22. The implantable, radio-opaque medical device of claim 18 wherein each Z is an ester of a carboxylic acid, wherein each ester group is independently selected from the group consisting of ethyl, butyl, hexyl, octyl, and benzyl groups.

23. The implantable, radio-opaque medical device of claim 22 wherein both $R_0$ and $R_{15}$ are (—$CH_2$—) and each Z is an ethyl ester of a carboxylic acid.

24. The implantable, radio-opaque medical device of claim 16 wherein A is:

$$-\overset{O}{\underset{\|}{C}}-.$$

(VIIIa)

$$\left\{\left(O-\underset{R_6}{\overset{R_5}{\underset{|}{\overset{|}{C}}}}-R_{15}-\overset{O}{\underset{\|}{C}}-NH-\underset{Z}{\overset{|}{CH}}-R_0-\underset{}{\overset{(X_2)_{Y2}}{\bigcirc}}-O-A\right)_{1-g}\left(O-\underset{R_{17}}{\overset{R_{16}}{\underset{|}{\overset{|}{C}}}}-R_0-NH-\underset{Z}{\overset{|}{CH}}-R_0-\bigcirc-O-A\right)_g\right\}$$

wherein:

(a) $R_5$, $R_6$, $R_{16}$, and $R_{17}$ are each independently selected from the group consisting of H, Br, I and straight and branched alkyl groups having up to 18 carbon atoms; provided that when g is zero, $R_5$ and $R_6$ are independently Br or I unless $R_{15}$ is —$CJ_1$-$CJ_2$-;

25. The implantable, radio-opaque medical device of claim 18 wherein A is:

$$-\overset{O}{\underset{\|}{C}}-R_8-\overset{O}{\underset{\|}{C}}-.$$

26. The implantable, radio-opaque medical device of claim 25 wherein $R_8$ is selected from the group consisting of saturated and unsaturated, substituted and unsubstituted alkyl groups containing up to 8 carbon atoms.

27. The implantable, radio-opaque medical device of claim 26 wherein $R_8$ is selected from the group consisting of —$CH_2$—C(=O)—, —$CH_2CH_2$—C(=O)—, CH=CH—, and (—$CH_2$—)$_Q$, wherein Q is between 0 and 8, inclusive.

28. The implantable, radio-opaque medical device of claim 25 wherein $R_8$ is selected from the group consisting of saturated and unsaturated, substituted and unsubstituted aryl and alkyaryl groups containing from 13 to 20 carbon atoms.

29. The implantable, radio-opaque medical device of claim 18 wherein said polymer further comprises one or more poly(alkylene oxide) blocks.

30. The implantable, radio-opaque medical device of claim 18 wherein $Y_2$ is 1 or 2.

31. The implantable, radio-opaque medical device of claim 18 wherein said medical device is formed from said polymer.

32. The implantable, radio-opaque medical device of claim 18 wherein said medical device is coated with said polymer.

33. The implantable, radio-opaque medical device of claim 18 wherein said device comprises a stent comprising said polymer.

34. The implantable, radio-opaque medical device of claim 31 wherein said device is a stent.

* * * * *

UNITED STATES PATENT AND TRADEMARK OFFICE
CERTIFICATE OF CORRECTION

PATENT NO.      : 7,056,493 B2                                        Page 1 of 1
APPLICATION NO. : 10/691750
DATED           : June 6, 2006
INVENTOR(S)     : Kohn et al.

It is certified that error appears in the above-identified patent and that said Letters Patent is hereby corrected as shown below:

On the title page, item [54] and column 1, line 1:

The title should read --RADIO-OPAQUE POLYMERIC BIOMATERIALS--

Columns 7-8, Formula VIIIa, that portion of the formula reading

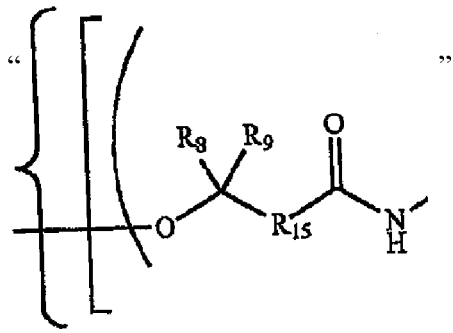

should read

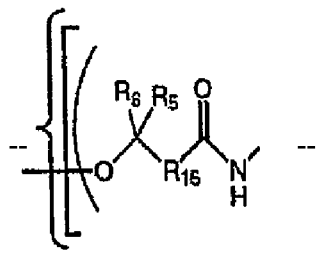

Columns: 24, 25, and 27,

Claim 3, line 9; Claim 4, line 9; Claim 11, line 3; and Claim 28, line 3, for the term "alkyaryl", each occurrence, should read -- alkylaryl --.

Signed and Sealed this

Twenty-seventh Day of February, 2007

JON W. DUDAS
*Director of the United States Patent and Trademark Office*

UNITED STATES PATENT AND TRADEMARK OFFICE
CERTIFICATE OF CORRECTION

PATENT NO. : 7,056,493 B2
APPLICATION NO. : 10/691750
DATED : June 6, 2006
INVENTOR(S) : Joachim B. Kohn et al.

It is certified that error appears in the above-identified patent and that said Letters Patent is hereby corrected as shown below:

At column 18, line 44, please replace "particles" with --articles--.

At column 19, line 21, please replace "particles" with --articles--.

At column 19, line 22, please replace "particles" with --articles--.

Signed and Sealed this

Thirtieth Day of March, 2010

David J. Kappos
*Director of the United States Patent and Trademark Office*